United States Patent [19]

Mast et al.

[11] Patent Number: 4,929,084
[45] Date of Patent: May 29, 1990

[54] MEASURING HEAD

[75] Inventors: Fred Mast, Wil; Jean A. Knus, Zurich, both of Switzerland

[73] Assignee: GRETAG Aktiengesellschaft, Regensdorf, Switzerland

[21] Appl. No.: 300,936

[22] Filed: Jan. 24, 1989

[30] Foreign Application Priority Data

Feb. 2, 1988 [CH] Switzerland .......................... 360/88

[51] Int. Cl.$^5$ ..................... G01N 21/27; G01N 21/47; G01J 3/10
[52] U.S. Cl. .................................... 356/446; 356/328
[58] Field of Search ............... 356/328, 419, 334, 445, 356/446, 447, 448; 250/226

[56] References Cited

U.S. PATENT DOCUMENTS

| | | | |
|---|---|---|---|
| 3,244,062 | 4/1966 | Sweet | 356/446 |
| 3,982,824 | 9/1976 | Rambauske | 350/294 |
| 4,025,200 | 5/1977 | Zeineh . | |
| 4,076,421 | 2/1978 | Kishner | 356/328 |
| 4,078,858 | 3/1978 | Mast | 356/446 |
| 4,093,991 | 6/1978 | Christie, Jr. et al. | 356/328 |
| 4,645,350 | 2/1987 | Weidmann et al. | 356/418 |
| 4,865,456 | 9/1989 | Mast et al. | 356/446 |

FOREIGN PATENT DOCUMENTS

| | | |
|---|---|---|
| 0242725 | 10/1987 | European Pat. Off. . |
| 3313668 | 10/1984 | Fed. Rep. of Germany . |
| 1527717 | 4/1968 | France . |
| 2181265 | 4/1987 | United Kingdom . |

OTHER PUBLICATIONS

Eine einfache Messanordnung zur photoelektrischen Spektrometrie moglichst kleiner Konzentrationen, M. Nordmeyer, Spectrochimica Acta, vol. 27B, No. 8, Aug. 1972, Pergamon Press (Northern Ireland).
Proceedings of the Society of Photo-Optical Instrumentation Engineers, vol. 240, "Periodic Structures, Gratings, Moire Patterns, and Diffraction Phenomena", Jun. 29–Aug. 1, 1980 San Diego, J. M. Lerner, Diffraction gratings ruled and holographic—a review, pp. 82–88.
Unterscheiden Kleinste Differenzen, H. Hencke, Feb. 27, 1987, pp. 29–39.
Patent Abstract of Japan, vol. 11, No. 370 (p. 642) (2817), Dec. 3, 1987—"Photoelectric Colorimeter Which Can Measure Density"—Japanese Patent Pub. No. 62-142240, Jun. 25, 1987.
Nouvelles Graphiques, vol. 37, No. 2, Jan. 1987, "La Nature Connait Ses Imperfections", Macbeth y pallie.

Primary Examiner—Vincent P. McGraw
Attorney, Agent, or Firm—Burns, Doane, Swecker & Mathis

[57] ABSTRACT

A measuring head, in particular a manual device for the determination of photometric data, includes an optical illuminating device with an aspherical mirror having a groove which extends in an annular manner around an axis of rotational symmetry of the groove, and which, in cross-section, has the configuration of an elliptical segment. The measuring optics to detect the light reflected from a measuring spot forms a round measuring spot on an ellipse at the inlet slit of a monochromator, for which a spherical/cylindrical lens, a first glass rod and a second glass rod are used, the glass rods being provided with cylindrical surfaces, the associated cylinder axes of which are crossed with each other.

13 Claims, 4 Drawing Sheets

MEASURING HEAD

BACKGROUND OF THE INVENTION

The invention relates to a measuring head for an apparatus to determine photographic data having a light source, an optical projection means to illuminate a measuring spot on a measuring surface, a spherical annular mirror, a flat annular mirror applied to a surface of a glass ring body and a measuring means.

A measuring head of this type having an optical projection means to illuminate a measuring surface and optical measuring means for measuring the light reflected is known from U.S. Pat No. 4,078,858 and comprises an incandescent lamp, which in order to produce a measuring spot, is associated with a collimator lens and a deviation mirror, together with a further collecting lens. The light reflected by the measuring spot at an angle of 45° arrives in the optical measuring means, which comprises a spherical annual mirror and a flat spherical mirror.

U.S. Pat. No. 3,982,824 teaches a mirror system for electromagnetic radiation or acoustic radiation, in which in order to avoid shadowing and chromatic aberration, a primary mirror cooperates with a secondary mirror. The mirror surfaces of the primary mirror are formed by a parabolic segment rotated around the optical axis as the generating line, wherein the parabolic focus describes a circular focal line in a radial plane with respect to the optical axis of the mirror system. The mirror surface of the secondary mirror of the mirror system is formed by the rotation of part of an ellipse around the system axis, wherein a first focal point of the ellipse remains on the optical axis, while the second focal point of the ellipse migrates in a circular focal line around the optical axis of the mirror system, when the ellipse is rotated. All axial rays impacting the primary mirror are collected in the known lens system in the focal point of the secondary mirror. Axial rays impacting the secondary mirror directly are reflected in the direction of the optical axis of the system and do not arrive in the focal point of the ellipse. Axial beams emanating from a point shaped source of radiation at a large distance from the known mirror system, are focused perfectly, so that the mirror system produces an error free image of such beams only.

A reflector layout to concentrate the radiation emanating from a rod shaped flash lamp on a rod extending parallel to the flash lamp and consisting of a laser material, is described in GB-A 2,181,265. The reflector layout of the optically pumped laser is in the form of a cylinder aligned parallel to the longitudinal axis of the flash lamp and the laser rod, said cylinder having essentially the shape of an ellipse in cross-section, the focal points and focal lines of which, respectively, are passing through the flash lamp and the laser rod. In order to avoid the shadowing occurring in the area of the principal apex of the ellipse, the cross-section of the ellipsoidal cylindrical reflector has a special configuration in the zone of the two principal apexes, in order to capture the light reflected by a normal ellipsoidal mirror at a dead angle and to reflect it to the intersection of the secondary axis of the ellipse with the mirror surface, or to capture it from there. This is obtained when a deviating ellipsoidal shape is provided in the area of the principal apex of the ellipse, the first focal point of which coincides with the longitudinal axis of the flash lamp or the laser rod, respectively, and the second focal point of which is located where the secondary axis of the principal ellipse intersects with the reflector surface. The cross-section of this cylindrical reflector is thus generated by the superposition of a principal ellipse with four secondary ellipses, wherein all of the ellipsoidal surfaces are located in the same plane.

An apparatus to determine the optical density of photographs described in U.S. Pat. No. 3,244,062, comprises a measuring head with an optical projection means, which images the light of an incandescent lamp on the photographic material and an optical measuring means which captures the light re-scattered essentially perpendicularly from the photographic surface by means of a deviating mirror transversely to the optical axis of the optical projection means and exposes the inlet aperture of a photoelectron multiplier with the aid of a lens. The optical projection means makes it possible to expose the measuring spot, at an angle of incidence of essentially 45° on all sides, to the light originating in the incandescent light in the measuring head. The optical projection means correlated with the incandescent lamp contains a spherical annular mirror, which surrounds the incandescent lamp, with the filament of said lamp extending along the optical axis of the spherical annual mirror. The light of the lamp passing from the spherical annular mirror parallel to the optical axis of the optical projection means is focused by means of a simple annular mirror onto the measuring surface. The quality of the optical projection means and the optical measuring device of the known apparatus is adequate for simple density measurements in the determination of optical reflection properties.

From U.S. Pat. No. 4,025,200 another optical projection device for the laser light of a densitometer or spectral photometer is known. The laser light is expanded, by means of a transparent tube aligned transversely to the direction of radiation, along a plane extending at right angles to the axis of the tube. After passing through a diaphragm, with the aid of a cylindrical lens, located transversely to the direction of expansion, the beam is narrowed, in order to produce a scanning beam, the width of which may be adjusted by altering the distance of the cylindrical lens to the object to be scanned.

The configuration of a spectral photometer with a simultaneous evaluation of the reflection spectrum of moving measuring surfaces is disclosed in U.S. Pat. No. 4,076,421. The light of a xenon flash lamp arrives in the inner space of an Ulbricht sphere provided with a coating for diffusely reflecting the light, in which the measuring surface of the sample to be scanned is also located. Through an aperture, the light reflected from the measuring surface arrives at a lens, which focuses it onto a slit. The slit is correlated with a concave reflection grating, which decomposes the light spectrally in a manner such that individual photodetectors of a linear array are exposed to light of different wavelengths. Because of the high light output of the xenon flash lamp, the intensity losses resulting from the diffuse reflection on the inside of the sphere are acceptable.

From FR-A 1,527,717 a portable reflectometer is known which comprises a measuring head with an incandescent lamp and an optical projection means, together with an optical measuring means. The light of the incandescent lamp exposes through a filter on the one hand, directly a first photoresistor, and on the other hand, by means of the projection device and the measuring means, a second photoresistor. The two photoresistors are located in a balancing bridge circuit, whereby the intensity of the light reflected by a measuring surface may be evaluated. The filament of the incandescent bulb in the measuring head is located in the focal point of a parabolic mirror, which comprises a recess for the filter to be inserted. The light leaving the parabolic mirrors essentially in the direction of the optical axis, arrives through a conical optical wave guide or collector made of a refracting material, at a coupling disk of a refracting material, the diameter of which is smaller than the diameter of the parabolic mirror and smaller than the opposing end of the conical collector. During measurements, the coupling disk is pressed solidly against the surface of the object to be examined, said object consisting in particular of food or agricultural products. Along its axis, the conical collector has a cylindrical bore in which a cylindrical glass rod is located. On the side facing the coupling disk, the glass rod has a flat frontal surface adhesively bonded to said coupling disk. On its other end, the glass rod has a spherical surface, the associated focal point of which is located on the surface of the refracting coupling disk, which may be pressed onto the measuring surface to be examined. Inside the bore in the conical collector, the second photoresistor is located, spaced apart from the spherical surface of the glass rod. The first photoresistor, which detects the intensity of the output light, is located on the reverse side of the photoresistor exposed to the measuring light. No spectral analysis is possible with this known portable reflectometer, but only an analysis of the reflection, using different replaceable filters.

SUMMARY OF THE INVENTION

Based on this state of the art, it is the object of the invention to provide a measuring head of the aforementioned type, whereby it is possible to pass the measuring light reflected from a measuring spot to a grid monochromator with adequate precision and intensity, in order to carry out a spectral analysis of the light reflected.

This object is attained relative to an optical illuminating means by a measuring head wherein a rotationally symmetrical, aspherical mirror is coordinated with the source of light, the mirror being provided on a side facing the light source with an annular groove having the cross-sectional configuration of an elliptical segment of an ellipse, a first focal point of which coincides with the location of the light source on the axis of rotational symmetry outside the aspherical mirror, and a second focal point of which is located laterally offset relative to the axis of rotational symmetry of the aspherical mirror, in an annular diaphragm surrounded by the spherical annular mirror, and the object of the invention is achieved relative to an optical-measuring device by a measuring head wherein the optical measuring means comprises a plurality of cylindrical lens surfaces, the correlated cylinder axes of which are at right angles to each other.

BRIEF DESCRIPTION OF THE DRAWINGS

Other objects and advantages of the present invention will become apparent from the following detailed description of preferred embodiments as described in conjunction with the accompanying drawings in which.

DETAILED DESCRIPTION OF THE PREFERRED EMBODIMENTS

Figure 1:
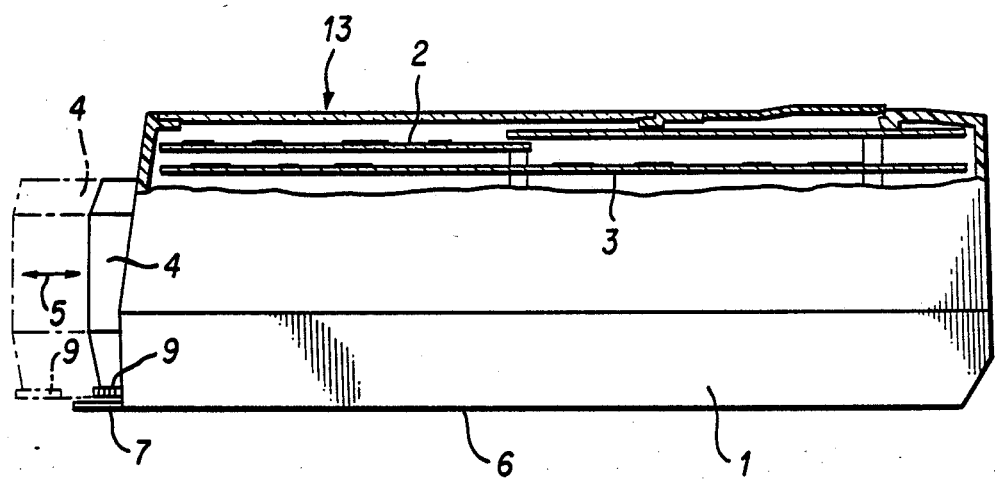
FIG. 1 shows a lateral elevation with a partial cross-sectional view of a manual device equipped with a measuring head according to the invention.

The device shown in a partially sectioned lateral elevation in FIG. 1 corresponds in its external dimensions to a manual reflector densitometer and is therefore compact in its configuration. However, in contrast to a conventional densitometer, the manual device shown in FIG. 1 makes it possible to determine reflection and density spectra and colorimetric data, in addition to densitometric values.

The manual device comprises a housing 1, in which one or several printed boards 2, 3 are provided for a measured data processing and control logic, which are shown schematically in the upper part of the sectioned housing 1.

From the left lateral wall of the housing 1 a measuring head is protruding. The measuring head may be displaced between a rest position shown by solid lines in FIG. 1 and a working position indicated by broken lines in FIG. 1, along a double arrow 5 parallel to the bottom 6 of the housing 1. In the retracted rest position a sight plate 7 projects over the edge of the measuring head 4, which may be seen most readily in FIG. 2. The slight plate 7 has a measuring diaphragm 8 which serves to indicate the position and size of a measuring spot 57 (FIG. 3) when the measuring head 4 is in the working position and to shield against scatter light.

Figure 2:
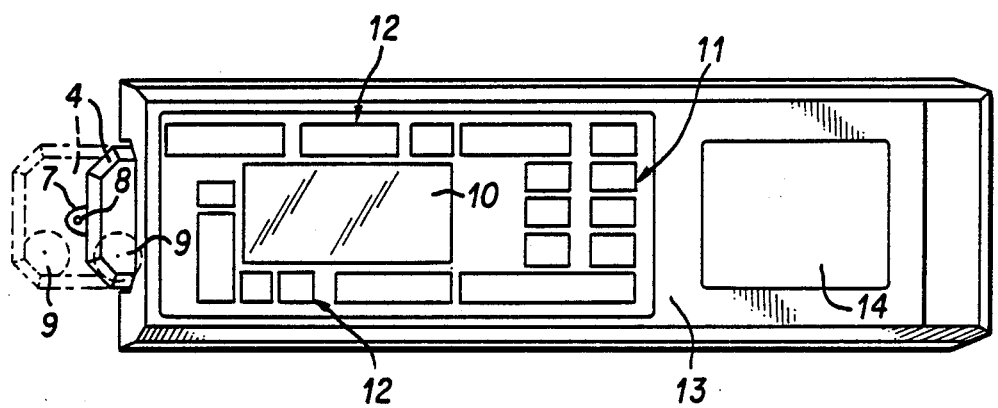
FIG. 2 shows a top elevation of the manual device.

If the measuring head 4 is moved from the rest position shown in FIGS. 1 and 2 into the working or measuring position shown by broken lines in FIGS. 1 and 2, the optically effective axis of the measuring head 4 passes exactly through the center of the measuring diaphragm 8.

In FIGS. 1 and 2, a filter wheel drive 9 is further shown, said drive being connected with a filter wheel provided in the measuring head 4 and making it possible to insert into the beam path of the measuring head 4, a polarizer to measure wet printed sheets, a D65 conversion filter to take fluorescence into account, or a diaphragm without a filter. The filter wheel drive 9 thus has three positions, which are set manually, but which are shown in a display field 10, for example a liquid crystal display.

The display field 10 also serves to show the measured values determined by the manual device in numerical form or in the form of spectra or bar diagrams. To operate the manual device around the display field 10, a row of keys of a keyboard 11 and several indicating fields 12 associated with the display field 10 are located. The display field 10, the keyboard 11 and the indicating fields 12 are located on the top side of the housing 1, with a wide surface measuring key 14 being provided on the side facing away from the measuring head for the actuation of the measuring process.

Figure 5:
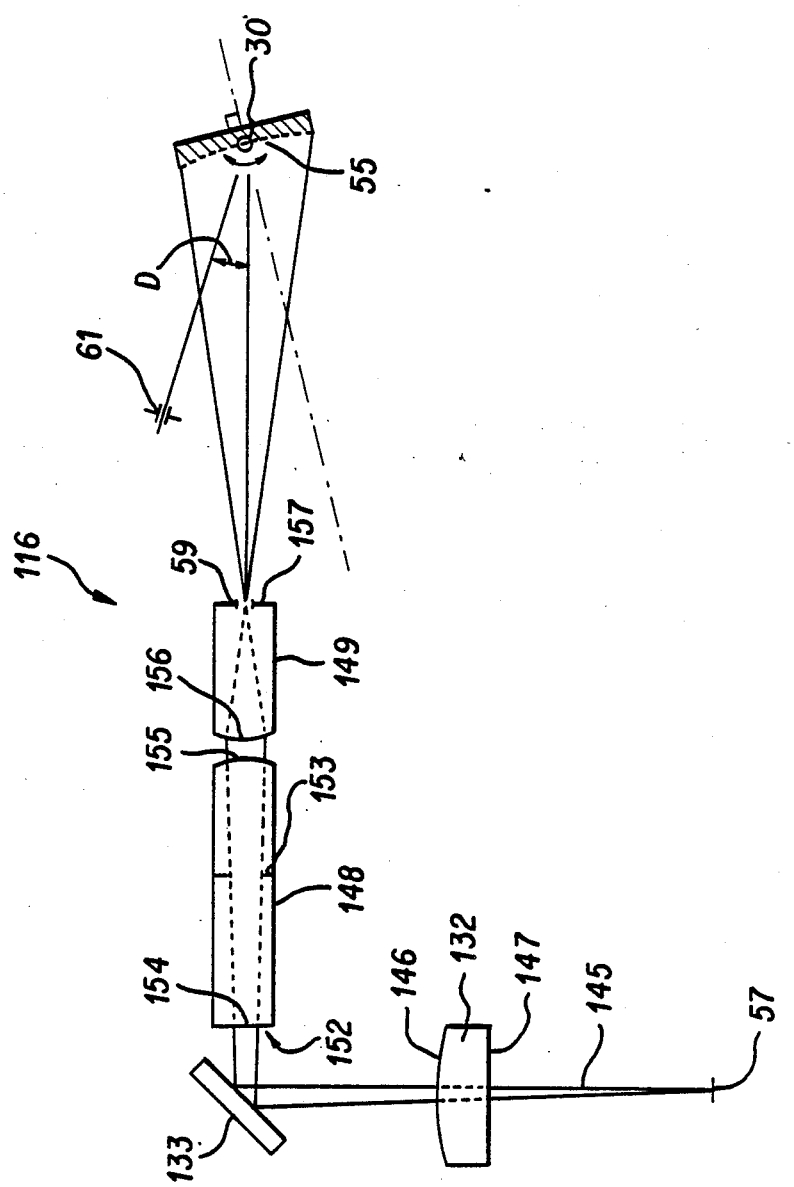

Upon the actuation of the measuring key 14, the data processing and control logic is activated to move the measuring head 4 from its rest position into the working position, in order to detect by means of a spectral chamber provided inside the housing 1, with a diffraction grating 55 shown in FIG. 5, the spectrum of the light reflected for example by a printed sheet on which the manual device is resting, at the location of the measuring diaphragm 8. The processing of the reflection spectrum is carried out by means of the data processing and control logic. Following the detection of the spectrum, the measuring head returns into its rest position, until a new measuring process is actuated by operating the measuring key 14.

The measuring head 4 is displaced by means of a measuring carriage, not shown, which is guided in a longitudinally mobile manner within the housing 1.

Figure 3:
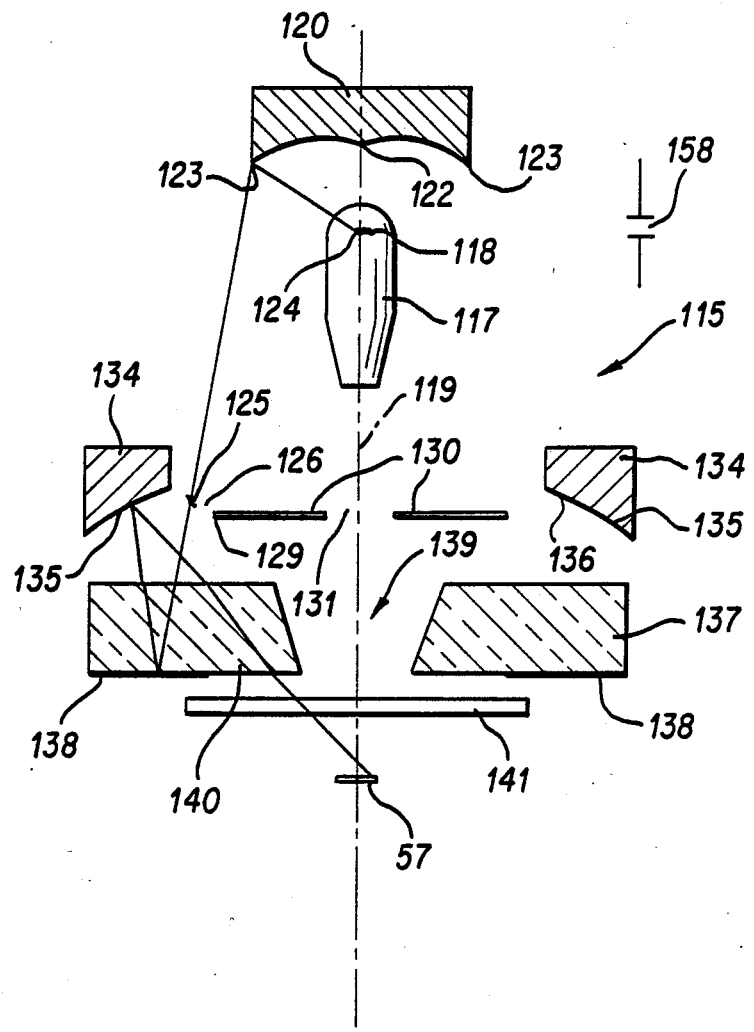
FIG. 3 shows a partial cross-sectional view of an exemplary embodiment of the optical illuminating means of the measuring head.

The measuring head 4 contains optical measuring means, which consist of the optical illuminating means 115 shown in FIG. 3 and the optical measuring means 116 shown in FIG. 5. The latter figure further shows the diffraction grating 55, the holder of which is fastened to a rotating grating shaft 30, in order to tune through the spectral range to be detected by rotating the grating shaft 30.

The optical means located in the measuring head 4 has the function on the one hand to illuminate the measuring spot 57, depicted in FIGS. 3 and 5 by a line, and on the other hand, to capture the light reflected from the illuminated measuring spot 57 and to project it onto the diffraction grid 55 for spectral decomposition. The illuminating optics shown in FIG. 3 makes it possible to expose the measuring spot 57, at an angle of incidence of essentially 45°±5° from all sides, to the light of an incandescent lamp 117, with the light being reflected from the measuring spot 57 into the measuring optics 116 for receipt at a measuring angle of essentially 0°±5°. The diameter of the measuring spot 57 amounts to 3 mm. The incandescent light emitted by the lamp 117 represents illumination with light of type A, with the incandescent lamp being configured so that it will provide the measuring light at the color temperature required.

The lamp 117 is placed in the measuring head 4 in a manner such that its filament 118 is located on the longitudinal or rotational axis 119 of the illuminating optics 115, which is laid out in a rotationally symmetrical fashion. In addition, the filament 118 is located in a first elliptical focal point correlated with an aspherical body 120, the aspherical body being shown in FIG. 3 above the lamp 117 and designed in a rotationally symmetrical fashion. The aspherical body 120 is mirrored on its side facing the lamp 117 and has the configuration as shown in the enlarged view of FIG. 4.

The mirrored side of the spherical body 120 facing the lamp 117, has an annular groove 121, extending around the axis of rotation 119, the inner edge of which forms a central elevation 122 located on the axis of rotation 119. An outer edge 123 of the groove 121 extends further downward in the direction of the lamp 117 than does the inner edge represented by the central elevation 122.

Figure 4:
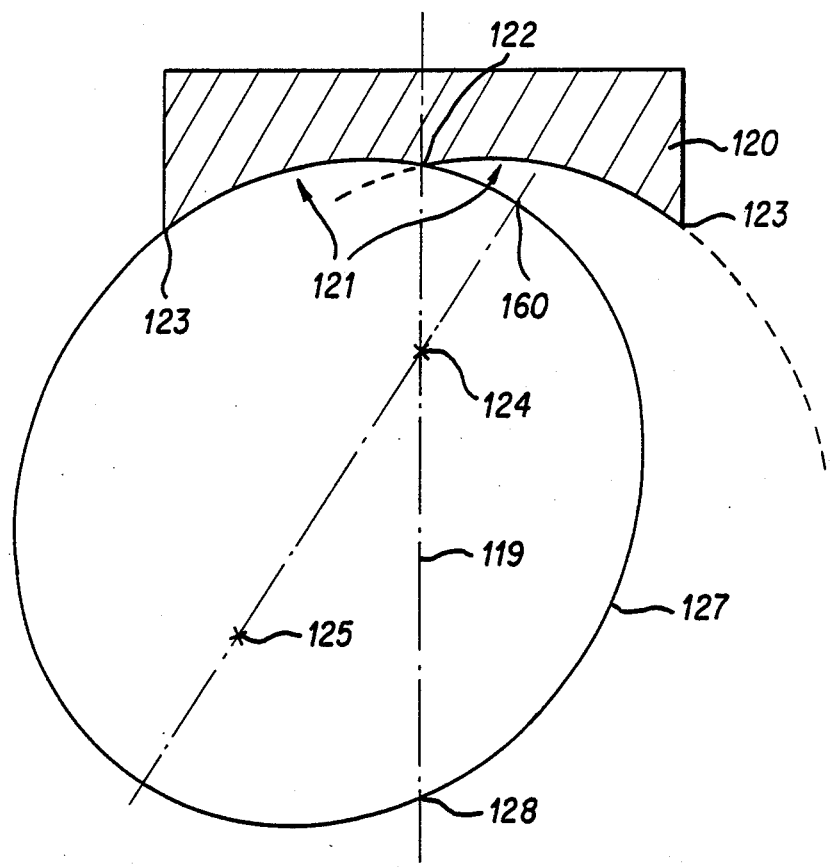
FIG. 4 shows a cross-sectional view of an aspherical mirror of the illuminating means, enlarged with respect to FIG. 3, to depict the configuration of the mirrored surface; and, FIG. 5 shows a partial cross-sectional view of an exemplary embodiment of the optical measuring means located in the measuring head and the fundamental configuration of an associated monochromator with a diffraction grating.

The groove 121 has the cross-sectional configuration of an ellipsoidal segment. FIG. 4 shows how the curve of the groove 121 is generated by placing an ellipse 127 with its first focal point 124 on the longitudinal center axis or axis of rotation 119 so that the second focal point 125 is spaced apart from the rotation axis 119. The position of the second focal point 125 is given by the distance of an annular aperture diaphragm 126, shown in FIG. 3. The groove 121 has a shape which is generated by rotating the ellipse 127 shown in FIG. 4 around the rotation axis 119, with the location of the focal point 124 and the location of the intersection 128 of the ellipse 127 with the rotation axis 119 shown in FIG. 4 remaining stationary in space upon a rotation of the ellipse 127. The form of the ellipse 127 is chosen so that the ratio of the distance between the apex 160 and the first focal point 124 on the one hand, and the apex 160 and the second focal point 125, on the other, is approximately 1:3.

The light reflected by the spherical body 120 passes through the aforementioned aperture diaphragm 126, which is formed around the circle defined by the second focal point 125 during the rotation of the ellipse 127. The diaphragm 126 is bordered at its inner edge 129 by a diaphragm ring 130, which has an aperture 131 for an optically conducting tube, not shown, which also serves to fasten the spherical/cylindrical lens 132 shown in FIG. 5 and a deviating mirror 133. By appropriately dimensioning the size of the square filament 118 (0.6×0.6 mm) of the lamp 117, practically all of the light of the incandescent lamp 117 emitted within a solid angle ±70° falls through the annular diaphragm 126, and thereby the optical efficiency of the illuminating optical means 115 is very high. This is important, as in this manner a lamp 117 with the lowest possible capacity of about 2 Watts may be used (battery powered operation).

The diaphragm ring 130 is coaxial with the rotating axis 119 and is surrounded by an annular glass body 134, which on its underside has a spherically curved, concave annular surface with a spherical annular mirror 135, applied by vapor deposition. The lower inner edge 136 of the annular glass body 134 forms the outer boundary of the aforementioned annular diaphragm 126.

Under the annular glass body 134, a glass ring body 137 is located, the center aperture 139 of which is conically narrowed in a direction away from the annular glass body 134. On its underside facing away from the glass body 134, the glass ring 137 is provided with a flat, annular mirror surface 138. Around the conical aperture 139, the glass ring 137 has an annular window 140 for the passage of light.

If a polarizer or another filter is inserted into the beam path of the measuring head 4, it replaces the polarizer 141 shown in FIG. 3. The measuring spot 57 may be seen in FIG. 3 under the glass ring 137 and the polarizer 141. The beam path of the light emitted by the lamp 117 is shown in FIG. 3 and indicates how the lamp light is reflected by the aspherical body 120 to the annular diaphragm 126. Following its passage through the diaphragm 126, the light traverses the glass ring 137 and is reflected by the annular mirror surface 138 in the direction of the spherical annular mirror 135 on the underside of the annular glass body 134. The spherical annular mirror 135 reflects the lamp light to the annular light passage window 140. After leaving the window 140 and passing through the optionally present polarizer 141, the lamp light impacts the measuring spot 57.

Persons skilled in the art will recognize that the imaging optics described above reproduces the spherical body 120 onto the measuring spot 57 in a manner such that the outer edge 123 of the aspherical body 120 is reproduced sharply on the edge of the measuring spot 57. The inner edge 122 is imaged unfocused in the center of the measuring spot 57. The distances and curvatures are chosen so that the measuring spot 57 has the desired size with a 3 mm diameter and the angle of illumination of 45°±5° is retained.

On the top right hand side of FIG. 3, in the vicinity of the lamp 117, a catcher diaphragm 158 is seen, which makes it possible to capture the light of the lamp 117 for monitoring.

The light reflected from the measuring spot 57 is captured by means of the measuring optics 116 (FIG. 5) and passed for spectral decomposition to the diffraction grating 55 and from there to a photodiode, not shown, which is connected through electronic circuits with the inlet of a computer to evaluate the spectral reflections.

The beam of light 145 reflected by the measuring spot 57 initially passes through the aforementioned spherical/cylindrical lens 132, the longitudinal axis of which is aligned with the rotation axis 119 (FIG. 3), prior to being diverted by the deviating mirror 133 at right angles to the rotation axis 119.

The spherical/cylindrical lens 132 has on its side facing the deviating mirror 133, a spherical surface 146 and on its underside facing the measuring spot 57 a cylindrical surface 147, with the associated cylinder axis extending at right angles to the grating shaft 30 of the diffraction grating 55 and parallel to the plane of the drawing and of the measuring spot 57.

The beam of light deflected by the mirror 133 initially passes through a first glass rod 148 and then through a second glass rod 149, prior to impacting the diffraction grating, with its width expanded to 0.75 mm in the direction transverse to the inlet slit 59. The diffraction grating 55 for the spectral decomposition of the light consists of a halographic concave reflection grating with 1250 lines/mm, which is optimized relative to its efficiency for blue. The configuration, shown schematically, corresponds to a monochromator.

At an angle D of 25°, the light reflected by the diffraction grating 55 passes to an outlet slit 61 with a width of 0.75 mm, and from there to the photodiode, not shown. In order to measure the entire spectrum, the diffraction grating 55 is rotated by the aforementioned grating shaft 30. The unfocused light produced by the width of the inlet slit 59, the outlet slit 61 and the rotation of the diffraction grating 55 in the course of the measurement, permits a spectral resolution of 10 nm. In order to slightly further improve the sharpness, the signal entered in the computer of the manual device is enhanced by a computer method, in the usual manner according to the science of imaging.

While the edge of the measuring spot 57 is circular, the edge of the beam of light impacting the inlet slit 59 has an elliptical configuration, in order to obtain the highest possible optical yield. By means of the specific mode of imaging by the optical components shown in FIG. 5, the round measuring spot 57 is reproduced on an ellipse, with the minor axis of the ellipse corresponding to the width of the inlet slit 59 of the monochromator. The major axis of the ellipse has a length of about 3 mm. For this purpose, the first glass rod 148 is provided not only with a first inlet slit diaphragm 152 and a second slit diaphragm 153 extending perpendicularly to the first slit diaphragm 152, but also with two crossed cylindrical surfaces 154 and 155. The first cylindrical surface 154 at the end of the first glass rod 148 facing the inlet diaphragm 152, is essentially curving relative to the paper plane of FIG. 5. The cylinder axis of the first cylindrical surface 154 is thus parallel to the rotation axis 119 of the measuring head 4 and the drawing plane of FIG. 5, and at a right angle to the grating shaft 30. The first slit diaphragm 152 is located in the position shown in FIG. 5. However, it is not visible in the drawing, as its edges are located above and below the plane of the drawing, i.e., the first slit diaphragm 152 extends in the plane of the drawing transversely to the direction of widening of the beam of light reflected by the deviating mirror 133.

The orientation of the second cylindrical surface 155 at the end of the first glass rod 148 facing the diffraction grating 55 is chosen so that the cylinder axis correlated with the cylindrical surface 155 extends parallel to a tilting axis associated with the grating shaft 30 of the diffraction grating 55.

The second glass rod 149 is again provided with a first cylindrical surface 156 and a second cylindrical surface 157, the associated cylinder axes of which are crossing each other, as in the case of the first glass rod 148. The second cylindrical surface 157 correlated with the inlet slit 59 is curving in the longitudinal direction of the cylindrical surface 157, so that the associated cylinder axis is extending transversely to the inlet slit 59.

By means of the sharp anamorphotic intermediate imaging of the round measuring spot 57 on the inlet slit 59 and the limitation of the aperture angles at the slit diaphragms 152 and 153, the entrance pupil of the measuring optics 116 is located at infinity, while the exit pupil of the optical measuring means is bounded by an edge of the diffraction grating 55. For this reason, and because the pickup spot is slightly larger than the illuminated spot, the measuring optics 116 is insensitive to distance within a certain range. This distance is defined as the distance between the optics and the sample being measured.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. Measuring head for an apparatus to determine photographic data comprising:
   a light source;
   an optical projection means to illuminate a measuring spot on a measuring surface;
   a spherical annular mirror;
   a flat annular mirror applied to a glass ring;
   an optical measuring means; and,
   a rotationally symmetrical, aspherical mirror coordinated with the source of light, said aspherical mirror being provided, on a side facing the light source, with an annular groove having a cross-sectional configuration of an elliptical segment of an ellipse, a first focal point of which coincides with a location of the light source on the axis of rotational symmetry of the asperical mirror, and a second focal point of which is located laterally offset relative to the axis of rotational symmetry of the aspherical mirror, in an annular diaphragm surrounded by the spherical annular mirror.

2. Measuring head according to claim 1, wherein the aspherical mirror, the flat annular mirror and the spherical annular mirror are aligned in a manner such that an outer edge of the aspherical mirror is imaged sharply on an edge of the measuring spot, while an inner edge of the groove of the aspherical mirror is reproduced in an unfocused manner at a center of the measuring spot.

3. Measuring head for an apparatus for the determination of photographic data comprising:
   an optical projection means to illuminate a measuring spot on a measuring surface, said optical projection means further including:
   a measuring light source;
   a spherical annular mirror; and
   a flat annular mirror applied to a glass ring; and,
   an optical measuring means, said optical measuring means including:
   a plurality of cylindrical lens surfaces having correlated cylinder axes which are at right angles to each other.

4. Measuring head according to claim 3, wherein the optical measuring means further comprises:
   a spherical/cylindrical lens located on a longitudinal axis of the spherical annular mirror and the flat annular mirror.

5. Measuring head according to claim 4, wherein the cylindrical surface of the spherical/cylindrical lens faces in a direction toward the measuring spot.

6. Measuring head according to claim 5, wherein a cylinder axis associated with the cylindrical surface of the spherical/cylindrical lens extends at a right angle with respect to a grating shaft and an inlet slit of a monochromator fed by the measuring head.

7. Measuring head according to claim 3, wherein a first glass rod is located in a path of the measuring light, said rod being provided at its ends with cylindrical surfaces, the associated cylinder axes of which are at right angles to each other.

8. Measuring head according to claim 6, wherein a first glass rod is located in a path of the measuring light, said rod being provided at its ends with cylindrical surfaces, the associated cylinder axes of which are at right angles to each other.

9. Measuring head according to claim 8, wherein, between the first glass rod and the inlet slit of the monochromator, a second glass rod is located in the path of the measuring light, said second glass rod having first and second cylindrical surfaces, with the first cylindrical surface of the second glass rod facing toward the inlet slit having an associated cylinder axis extending at a right angle to the inlet slit of the monochromator, while the second cylindrical surface of the second glass rod has an associated cylinder axis extending parallel to the cylinder axis of the adjacent cylindrical surface of the first glass rod.

10. Measuring head according to claim 9, wherein a first slit diaphragm is provided at a light inlet end of the first glass rod, and a second slit diaphragm is provided inside the first glass rod, said first and second slit diaphragms being provided at right angles to said first glass rod and extending parallel to the inlet slit.

11. Measuring head according to claim 10, wherein a round measuring spot is reproduced by the optical measuring means on an ellipse, the long axis of which extends in a direction toward the monochromator and the short axis of which corresponds to the width of the inlet slit.

12. Measuring head according to claim 6, wherein a round measuring spot is reproduced by the optical measuring means on an ellipse, the long axis of which extends in a direction toward the monochromator and the short axis of which corresponds to the width of the inlet slit.

13. Measuring head according to claim 11, wherein the entrance pupil of the optical measuring means lies at infinity, while the exit pupil of the optical measuring means is bounded by an edge of a diffraction grating of the monochromator.

* * * * *